(12) United States Patent
Soliman Hussein et al.

(10) Patent No.: US 8,968,729 B2
(45) Date of Patent: Mar. 3, 2015

(54) DATE PIT COMPOSITION FOR THE TREATMENT OF ANIMALS

(75) Inventors: Ahmed Soliman Hussein, Al-Ain (AE); Ibrahim Hassan Belal, Al-Ain (AE); Salem Rashed Ali Alyalyali, Al-Ain (AE); Khaled Abas El-Tarabily, Al-Ain (AE)

(73) Assignee: United Arab Emirates University, Al-Ain (AE)

( * ) Notice: Subject to any disclaimer, the term of this patent is extended or adjusted under 35 U.S.C. 154(b) by 0 days.

(21) Appl. No.: 13/284,173

(22) Filed: Oct. 28, 2011

(65) Prior Publication Data

US 2013/0108615 A1    May 2, 2013

(51) Int. Cl.
| | | |
|---|---|---|
| A23K 1/14 | (2006.01) | |
| A23K 1/00 | (2006.01) | |
| A23K 1/16 | (2006.01) | |
| A23K 1/18 | (2006.01) | |
| A23K 1/10 | (2006.01) | |
| A23K 1/175 | (2006.01) | |

(52) U.S. Cl.
CPC ............... *A23K 1/146* (2013.01); *A23K 1/007* (2013.01); *A23K 1/1643* (2013.01); *A23K 1/1806* (2013.01); *A23K 1/1813* (2013.01); *A23K 1/1826* (2013.01); *A23K 1/184* (2013.01); *A23K 1/188* (2013.01); *A23K 1/106* (2013.01); *A23K 1/14* (2013.01); *A23K 1/1603* (2013.01); *A23K 1/1634* (2013.01); *A23K 1/164* (2013.01); *A23K 1/1758* (2013.01)
USPC ........................................................ 424/115

(58) Field of Classification Search
USPC ........................................................ 424/115
See application file for complete search history.

(56) References Cited

U.S. PATENT DOCUMENTS 4,428,969 A * 1/1984 Muller et al. .................. 426/53

FOREIGN PATENT DOCUMENTS

| CN | 1192329 A | 9/1998 |
| WO | 96/37116 A1 | 11/1996 |

OTHER PUBLICATIONS

Belal IEH. Evaluating fungi-degraded date pits as a feed ingredient for Nile tilapia *Oreochromis niloticus* L. Aquaculture Nutrition. 2008;14:445-452.*
Flemming JS. Use of mannanoligosaccharides in broiler feeding. Brazilian Journal of Poultry Science. 2004;6(3):159-161.*
Hussein AS. The use of dates and date pits in broiler starter and finisher diets. Bioresource Technology. 1998;66:219-223.*
Oyofo et al. Prevention of *Salmonella typhimurium* colonization of broilers with D-mannose. Poult Sci. 1989;68(10):1357-60.*
Landais E. Research raises hope for drug-free chicken meat. GulfNews. 2010;1-3.*
Van Metre D. Q fever. Colorado State University Extension. 2010;1-2.*
MOS. Mannanase (beta-mannanase preparation). VTR. 2011;1-4.*
Emmanuelle Landais, "Research Raises Hope for Drug-Free Chicken Meat." Gulf News, published Oct. 30, 2010, http://gulfnews.com/news/gulf/uae/environment/research-raises-hope-for-drug-free-chicken-meat-1.703781, 4 pages.
"Date Pits Tested As Antibiotic Replacement." The Poultry Site, published Apr. 7, 2011, http://www.thepoultrysite.com/poultrynews/22375/date-pits-tested-as-antibiotic-replacement, 3 pages.
Megan Detrie, "Researchers Test Date Pits As Replacement for Antibiotics." The National, published Apr. 7, 2011, http://www.thenational.ae/news/uae-news/science/researchers-test-date-pits-as-replacement-for-antibiotics, 2 pages.
"Date Pit As Poultry Antibiotic Concept to Be Patented in UAE." World Poultry, published Apr. 13, 2011, http://www.equimex.com/contact-us/linkedin/2003-date-pit-as-poultry-antibiotic-concept-to-be-patented-in-uae.html, 2 pages.
"Date Pits Concept to Be Patented for Anti Bacterial Properties." All About Feed, published Apr. 8, 2011, http://www.allaboutfeed.net/news/date-pits-concept-to-be-patented-for-anti-bacterial-properties-5456.html , 2 pages.
E. Bauza et al., "Date Palm Kernel Extract Exhibits Anti-aging Properties and Significantly Reduces Skin Wrinkles." International Journal of Tissue Reactions, vol. 24, No. 4, Jan. 1, 2002, pp. 131-136.
M. Khiyami et al., "Influence of Complex Nutrient Sources: Dates Syrup and Dates Pits on *Lactococcus lactis* Growth and Nisin Production." Journal of Biotechnology, vol. 136S, Oct. 1, 2008, p. S736.
H. Najib et al., "Effect of Enzymatic Treatment of Saudi Date Pits on Performance of Single Comb White Leghorn Hens and the Fatty Acid Profile of Their Eggs." International Journal of Poultry Science, vol. 11, No. 10, 2012, pp. 624-629.
European Search Report, European Application No. 12190250.6, dated Mar. 25, 2013, 8 pages.
A. Aldhaheri, et al., "Chemical Composition of Date Pits and Reproductive Hormonal Status of Rats Fed Date Pits." Food Chemistry, vol. 86, 2004, pp. 93-97.
J.W. Bennet, et al., "Use of Fungi Biodegradation." Manual of Environmental Microbiology, Editor in Chief Christon J. Hurst, ASM Press Washington, D.C., 2002, pp. 960-971.
Souhail Besbes, et al., "Date Seeds: Chemical Composition and Characteristic Profiles of the Lipid Fraction. " Food Chemistry, vol. 84, 2004, pp. 577-584.
Jonathan Gressel, et al., "Morphogenesis in Trichoderma: Photoinduction and RNA." Developmental Biology, vol. 15, 1967, pp. 575-598.

(Continued)

*Primary Examiner* — Ruth Davis
*Assistant Examiner* — Lynn Y Fan
(74) *Attorney, Agent, or Firm* — Fitch Even Tabin & Flannery LLP

(57) ABSTRACT

A method of treating or preventing bacterial infection in an animal comprises administering an effective amount of degraded date pits. Degraded date pits can be produced by the treatment of date pits with fungi.

15 Claims, 1 Drawing Sheet

(56) References Cited

OTHER PUBLICATIONS

B.S. Kamel, et al. "Nutritional Value of Whole Dates and Date Pits in Broiler Rations." Poultry Science, vol. 60, 1981, pp. 1005-1011.

Seema Patel, et al., "Functional Oligosaccharides: Production, Properties and Applications." World Journal of Microbiology and Biotechnology, 2011, vol. 27, pp. 1119-1128.

J.M. Vandepopuliere, et al., "Dates and Date Pits as Ingredients in Broiler Starting and Coturnix Quail Breeder Diets." Poultry Science, vol. 74, 1995, pp. 1134-1142.

F. Vinale, et al., "Major Secondary Metabolites Produced by Two Commercial Trichoderma Strains Active Against Different Phytopathogens." Letters in Applied Microbiology, vol. 43, 2006, pp. 143-148.

Francesco Vinale, et al., "Trichoderma-Plant-Pathogen Interactions." Soil Biology & Biochemistry, vol. 40, 2008, pp. 1-10.

Biggs, P., et al., "The Effects of Several Oligosaccharides on Growth Performances, Nutrient Digestibilities, and Cecal Microbial Populations in Young Chicks." Poultry Science, 2007, vol. 86, No. 11, pp. 2327-2336, abstract only.

Chahal, D.S. "Solid-State Fermentation with *Trichoderma reesei* for Cellulase Production." Applied and Environmental Microbiology, Jan. 1985, vol. 49, No. 1, pp. 205-210, abstract only.

Chahal, Parminder S., et al., "Production of cellulase in solid-state fermentation with *Trichoderma reesei* MCG 80 on wheat straw." Applied Biochemistry and Biotechnology, 1996, vol. 57-58, issue 1, pp. 433-442, abstract only.

Kumprecht, I., et al., "Effects of Dietary Mannanoligosaccharide Level on Liveweight and Feed Efficiency of Broilers." Abstract No. S118, Supplement to vol. 76, Issue 1, Jan. 1997, Journal of Poultry Science, p. 132.

Latifian, Maryam, et al., "Evaluation of culture conditions for cellulase production by two *Trichoderma reesei* mutants under solid-state fermentation conditions." Bioresource Technology, vol. 98, issue 18, Dec. 2007, pp. 3634-3637, abstract only.

Novak, Curtis, et al., "Use of Bio-Mos® to Control *Salmonella* and *Campylobacter* in Organic Poultry." Department Animal and Poultry Sciences, Virginia Tech, Blacksburg, Virginia, <http://www.zootecnicainternational.com/article-archive/nutrition/563-use-of-bio-mosr-to-control-salmonella-and-campylobacter-in-organic-poultry-.html> Jul. 1, 2007, 5 pages.

Singhania, Reeta Rani, et al., "Solid-state fermentation of lignocellulosic substrates for cellulase production by *Trichoderma reesei* NRRL 11460." Indian Journal of Biotechnology, vol. 5, (Suppl), Jul. 2006, pp. 332-336.

\* cited by examiner

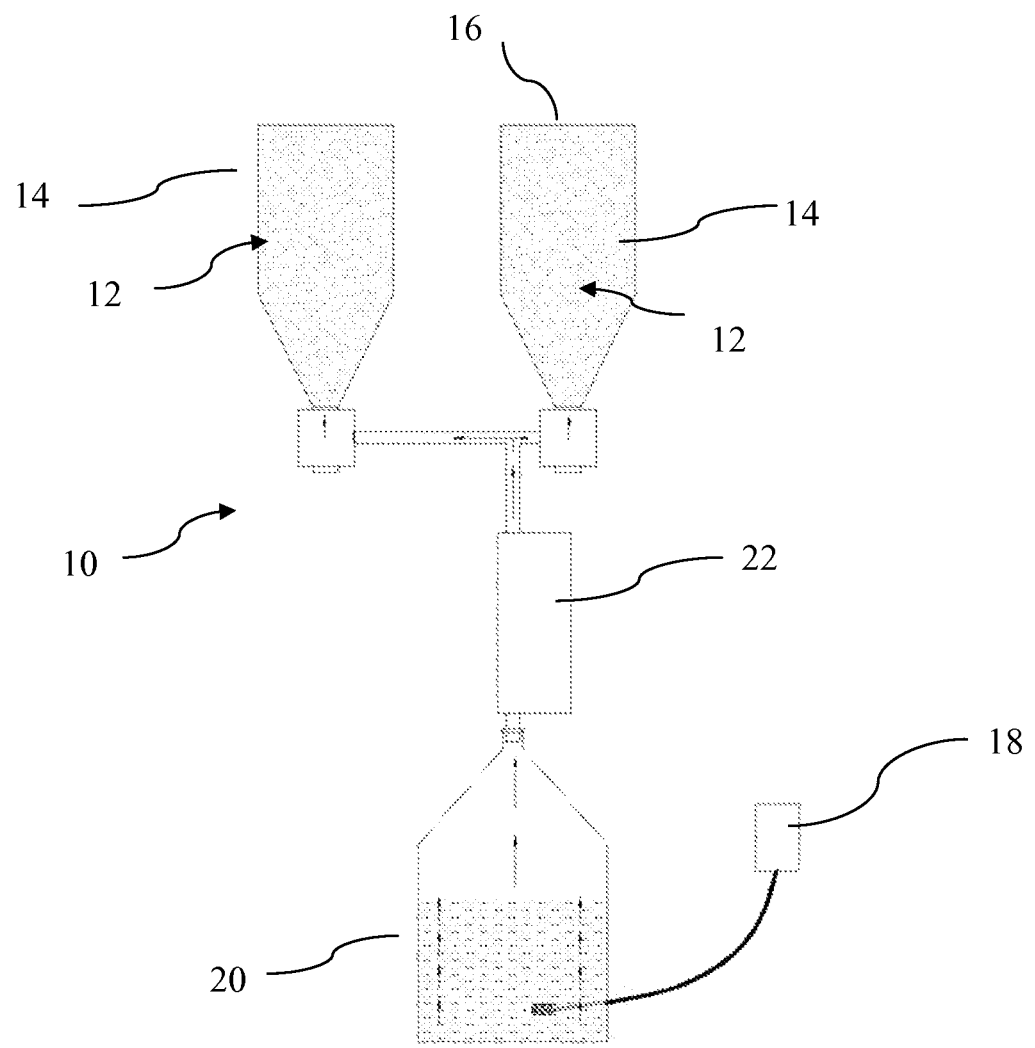

DATE PIT COMPOSITION FOR THE TREATMENT OF ANIMALS

This invention relates to compositions for treating and preventing bacterial infections in an animal. In particular the invention relates to compositions comprising degraded date pits.

BACKGROUND OF THE INVENTION

Sub-therapeutic doses of antibiotics have routinely been administered to animals in order to promote weight gain in apparently healthy animals. While supplementing animal feed with antibiotics can have a number of benefits, concerns exist over the use of conventional antibiotics in animal feed and water. The use of antibiotics in sub-therapeutic levels in animals has been implicated in the rise in antibiotic resistance of bacteria. Additionally, residual antibiotics may remain in meat products that are meant for human consumption.

To address these concerns the US Food and Drug agency (FDA) require that that antibiotic must be withdrawn from the feed of the animal at least two weeks prior to slaughter to prevent antibiotics remaining in the animal that is to enter the human food chain. The European Union and other countries require that antibiotics are not used as growth promoters in animal feed. Furthermore feed composition costs make a large proportion of the costs in animal production.

Date pits are readily available in a number of countries. Date pits have typically been seen as waste product from the preparation of dates and are usually discarded.

SUMMARY OF THE INVENTION

An object of the invention is to provide methods and compositions to treat and prevent bacterial infections in domestic animals.

A further object of the invention is to provide an alternative to conventional antibiotics to treat and prevent bacterial infections in domestic animals.

In one aspect, the invention comprises a method of treating and preventing bacterial infection in animals comprising: administering an effective amount of a degraded date pit composition to the animal.

The method includes administering the degraded date pit composition in an effective amount thereby preventing or delaying the onset of a bacterial infection in the animal, or reducing the microbial load in the animal or inhibiting the growth or killing bacterium in the animal. The methods allow a reduction in the amount of conventional antibiotics that will need to be administered to maintain animal health.

The degraded date pit composition can be administered as a component of an animal feed composition. The animal feed can comprise between 5-20% (w/w) of a degraded date pit composition. Preferably the animal feed can comprise approximately 10% (w/w) of a degraded date pit composition.

The degraded date pit composition can comprise mannan-oligosaccharides (MOS) and/or comprise free mannose.

Bacterial infection may be caused by *Salmonella, Campylobacter, Shigella* or *Escherichia coli*.

The method can be used for treating an animal selected from the group consisting of cattle, horses, pigs, goats, fish and poultry. Preferably the animal is poultry.

A further aspect of the invention comprises an antibacterial feed additive for animals comprising degraded date pits.

The degraded date pits can be fungi treated date pits.

The antibacterial feed additive can be in the form of a powder.

A further aspect of the invention comprises an animal feed composition comprising the antibacterial feed additive as described. The degraded date pits provide an inexpensive antibacterial additive in use in an animal feed composition.

The animal feed comprises 5-20% (w/w) of the feed additive. Preferably the animal feed can comprise 10% (w/w) of the feed additive.

The animal feed can be a soy-corn based feed. The animal feed may comprise a blend of corn, soybean meal, vitamins, minerals, amino acids, corn oil and fish meal.

A further aspect of the invention comprises a method of producing an antibacterial feed stuff for treating and preventing bacterial infection in animals, the method comprising: treating date pits with a fungus to form a degraded date pit composition; and mixing the degraded date pit composition with an animal feed.

The degraded date pit composition can be mixed into the feed composition at a concentration of 5-20% (w/w). The degraded date pit composition can be mixed in the feed composition at a concentration of 10% (w/w).

Treating the date pits with a bacteria can comprise incubating the date pits and fungus together. The fungus used to treat the bacteria can be *Trichoderma reesei*.

BRIEF DESCRIPTION OF THE DRAWINGS

FIG. 1 shows a schematic view of a Solid State Degradation system.

DETAILED DESCRIPTION OF THE INVENTION

The invention comprises methods and compositions for treating and preventing bacterial infections in animals. The composition comprises degraded date pits which are administered to animals in an effective amount to treat or prevent bacterial infection. In some embodiments the animal will already have an infection and the degraded date pit composition is administered to treat the bacterial infection or reduce the bacterial load. In other embodiments the animal may not have an infection e.g. the degraded date pit composition is administered to prevent or delay the onset of a bacterial infection in the animal.

The term "degraded date pit" refers to a composition wherein date pits have been treated such that dietary fibres in the date pits are broken down into their digestible units.

One method for obtaining degraded date pit comprises treating date pits with a fungus to obtain a degraded date pit composition. A fungus suitable for degrading date pits is *Trichoerma reesei*. Other fungus, such as yeast, and which are capable of breaking down indigestible fibres found in date pits into digestible units can also be used. *Trichoerma reesei* can degrade date pits by breaking down mannan fibre into different products such as free mannose and mannan-oligosacchrides (MOS). Other fibres that *Trichoerma reesei* can break down into their digestible units include lignin, cellulose and hemicelluloses.

The date pits can be treated within a solid state degradation system by incubating the fresh dates in the presence of *Trichoerma reesei* under conditions suitable to promote degradation of the date pits. A solid state degradation system 10 as exemplified in FIG. 1 can be used to process the date pits. The date pits and fungi 12 are layered within a series of cones 14. Each cone 14 is closed by a cover 16, to avoid contamination. Preferably the cover is a fibre glass cover. During incubation air is blown from an air supply 18 into a water tank 20. The moist air created is then supplied to the cones 14. A disinfection unit 22 treats the moist air before it is supplied to the cones.

Once a degraded date pit composition is obtained it can be mixed with conventional animal feed ingredients to produce a supplemented animal feed composition having antibacterial properties.

The term "feed composition", refers to a preparation providing nutritional value to the animal. Preferred animals include cattle, pigs, goats, sheep, fish, horses, and poultry such as chickens, turkey, ducks, geese, ostriches, quails, pheasants or other domestic fowl. Preferably the animal being treated is poultry.

Any conventional animal feed composition may be supplemented with the degraded date pit composition. An animal feed can comprise a blend of corn, soybean meal, limestone, salt, dicalcium phosphate, vitamins, minerals, amino acids (such as DL-methionine and lysine), corn oil, fish meal. The feed composition can comprise further components such as further amino acids, enzymes and other nutritional components. The feed composition can be prepared by mixing the ingredients together in the required portions. The feed composition can comprise different portions of ingredients depending on the age of the animal the composition is being fed to. Thereby, having different feed compositions administered at different stages of the animal's life.

The degraded date pits can be added to the feed composition during the manufacture of the feed composition. The degraded date pits can be mixed with the conventional ingredients used in animal feeds or the degraded date pits can replace all or a portion of the conventional animal feed. For example a portion of the corn or soy component can be replaced with an equivalent amount of degraded date pits.

Alternatively the degraded date pit composition may be an additive added to a pre-formulated feed composition prior to feeding of the feed composition to the animal.

The degraded date pit composition can be in the form of a powder.

The degraded date pit composition is present in the feed at a concentration, or administered in an effective amount which provides an antibacterial effect in the animal. An effective amount refers to an amount of the degraded date pit composition which is effective, upon single or multiple dose administration to a subject, in treating or preventing a bacterial infection beyond that than would have been expected in the absence of such a treatment.

The term "antibacterial effect" refers to the ability of the degraded date pit composition to preventing or delaying the onset of a bacterial infection in animal, to reducing the microbial load in animals and/or to inhibit the growth or kill bacterium in the animals. Exemplary bacterial pathogens include *Escherichia coli*, *Shigella* spp., *Salmonella* spp., *Camplyobacter* spp.

The degraded date pit composition can be present in the feed at a concentration which provides an equivalent antibacterial effect as that achieved by the use of conventional antibiotic supplemented feed, such as a feed supplemented with oxytetracycline.

The present invention is illustrated by the following example and is provided for exemplification purposes only. The particular examples, materials, amounts, and procedures are not intended to limit the scope of the invention.

EXAMPLE

Preparation of Fungus Culture

*Trichoderma reesei* is grown on potato dextrose agar (PDA) at 25+2° C. for 7 days in the dark.

To confirm that the fungi could degrade the date pits a ground date pits based inoculum was prepared by adding half a kilogram of ground date pits and 150 ml of distilled water into 1 liter flasks. The flasks were autoclaved at 121° C. for 30 min on 3 consecutive days. Under aseptic conditions the ground date pits were then inoculated with 8 agar plugs (6 mm diameter) from actively growing margins of the *Trichoderma reesie* colony. The flasks were incubated at 25+2° C in the dark for three weeks. The flasks were shaken occasionally to ensure uniform colonisation of the date pits by the fungi. Colonized ground date pits which had been autoclaved twice served as a control.

Small amounts of the colonised and control ground date pits were plated onto PDA to confirm that *T. Reesei* was present or absent, respectively.

Preparation of Fungi-degraded Date Pits

Fungi-degraded date pits were produced using a Solid State Degradation (SSD) system inside an incubator.

Date pits of Phoenix dactylifera dates were crushed and grounded using a medium size mill (Skiold Saeby9300, Denmark) to reduce the size of the pits to about 1 mm in diameter. The ground date pit substrate was mixed, cleaned and sterilized three times at 121° C. for 30 minutes.

Sterilized date pit substrate was added to each cone of the SSD system. The starter culture of the fungus, *Trichoderma reesei*, prepared on PDA as described above, was added to each cone of the SSD system containing some of the sterilized date pit substrate. Further fungi cultures and sterilized date pits were added in layers until the volume of fungi and date pits reached 8 litres per cone. The cones are covered in order to avoid any contamination.

A continuous supply of moistened air is supplied to the SSD system. An Aquafine Ultra violet disinfection system provided the fungi and date pits with disinfected moist air during the incubation period. The SSD system is kept within a darkened room at a relative humidity of 90% and a temperature of 30° C. over a 3 week period.

At the end of the 3 week period the process was stopped and the degraded date pits with the fungi mass was collected and transferred to a refrigerator and kept at 4° C. until use in the feed.

Preparation of Poultry Feed

Six isocaloric-isonitrogenous diets were prepared. The diets were prepared as described in Table 1 (starter diet) and Table 2 (finisher diet).

All feed ingredients were ground to a suitable size and mixed in a commercial mixer for 20 minutes. Vitamin and mineral premixes, fish meal and oil were gradually added with continuous mixing the wet mix was then pass through a commercial mixer for 15 minutes for a homogenous distribution of the nutrients and particle sizes. The feed containing the degraded date pits were stored until use at 4° C.

For those feed containing the degraded and non degraded date pits, the date pit additive was added to the feed alongside the vitamin and mineral premixes. The degraded date pits were prepared as described above.

Prevention of Pathogenic Infections

To illustrate the effect of degraded date pit based feed on pathogenic infections in poultry two hundred, day old chickens were divided into six groups. Each chicken was housed in separate cleaned and sanitized Petersime brooding battery cages and kept in a well cleaned and disinfected poultry house. Water and feed were provided on an ad libitum basis.

Each group was fed with a different feed composition as follows:
1. Group 1 (control)—corn soy diet
2. Group 2 (control)—corn soy diet+antibiotic added (oxytetracycline 20%, 50 g/100 kg)
3. Group 3—5% non-degraded date pits corn-soy diet
4. Group 4—10% non-degraded date pits corn-soy diet
5. Group 5—5% degraded date pits corn-soy diet
6. Group 6—10% degraded date pits corn-soy diet The trial was divided into two periods. Period one (the starter period) started from day 1 to day 21. Period two (the finisher period) started from date 22 to day 33.

During the starter period the chickens were feed a diet having the following composition:

TABLE 1

| Ingredient Name | Control (kg) | 5% non degraded date pits (kg) | 10% non degraded date pits (kg) | 5% degraded date pits (kg) | 10% degraded date pits (kg) |
|---|---|---|---|---|---|
| Yellow corn | 59.4 | 53.7 | 46.6 | 53.7 | 46.6 |
| Soybean meal | 32 | 30.76 | 31.25 | 30.76 | 31.25 |
| Salt | 0.4 | 0.38 | 0.38 | 0.38 | 0.38 |
| Limestone | 1.1 | 1.05 | 1.1 | 1.05 | 1.1 |
| Dicalcium phosphate | 1.56 | 1.22 | 1.2 | 1.22 | 1.2 |
| Vitamin and Mineral Premix | 1 | 1 | 1 | 1 | 1 |
| DL-Methionine | 0.24 | 0.24 | 0.25 | 0.24 | 0.25 |
| Lysine | — | 0.1 | 0.1 | 0.1 | 0.1 |
| Corn oil | 2 | 3.35 | 5.02 | 3.35 | 5.02 |
| Fish meal | 2.3 | 3.2 | 3.1 | 3.2 | 3.1 |
| Non-Degraded Date pits | — | 5 | 10 | — | — |
| Degraded Date pits | — | — | — | 5 | 10 |

During the finisher period the chickens were feed a diet having the following composition:

TABLE 2

| Ingredient Name | Control (kg) | 5% non degraded date pits (kg) | 10% non degraded date pits (kg) | 5% degraded date pits (kg) | 10% degraded date pits (kg) |
|---|---|---|---|---|---|
| Yellow corn | 64.6 | 58.25 | 52.14 | 58.25 | 52.14 |
| Soybean meal | 28.4 | 27.72 | 26 | 27.72 | 26 |
| Salt | 0.42 | 0.36 | 0.33 | 0.36 | 0.33 |
| Limestone | 1.33 | 1.22 | 1.15 | 1.22 | 1.15 |
| Dicalcium phosphate | 1.05 | 0.95 | 0.8 | 0.95 | 0.8 |
| Vitamin and Mineral Premix | 0.2 | 0.2 | 0.2 | 0.2 | 0.2 |
| DL-Methionine | 0.2 | 0.2 | 0.3 | 0.2 | 0.3 |
| Lysine | 0.1 | 0.1 | 0.18 | 0.1 | 0.18 |
| Corn oil | 2.5 | 4.05 | 5.9 | 4.05 | 5.9 |
| Fish meal | 1.2 | 1.95 | 3 | 1.95 | 3 |
| Non-Degraded Date pits | — | 5 | 10 | — | — |
| Degraded Date pits | — | — | — | 5 | 10 |

At the end of the trial period microbial population densities in dry chicken gut tissue were determined for: total bacterial counts, *Salmonella* spp., *Camplylobacter* spp., *Shigella* spp. and *Escherichia coli*.

Microbial population densities in log 10 colony-forming units/g dry chicken gut were determined by the serial dilution tenfold plate assay. The results are shown in Table 3.

TABLE 3

| Treatments | Population density (mean $\log_{10}$ cfu per g dry gut tissue) | | | | |
|---|---|---|---|---|---|
| | Total bacterial counts | *Salmonella* spp. | *Campylobacter* spp. | *Shigella* spp. | *Escherichia coli* |
| (1) Control (without antibiotics) | $8.53 \pm (0.88)^a$ | $2.03 \pm (0.13)^a$ | $2.74 \pm (0.09)^a$ | $2.12 \pm (0.07)^e$ | $7.19 \pm (0.14)^a$ |
| (2) Control With antibiotics | $4.21 \pm (0.14)^b$ | $0.03 \pm (0.03)^b$ | $0.08 \pm (0.05)^b$ | $0.53 \pm (0.06)^b$ | $2.06 \pm (0.18)^b$ |
| (3) With 5% un-degraded date pits | $7.07 \pm (0.91)^c$ | $1.41 \pm (0.08)^c$ | $2.01 \pm (0.10)^c$ | $1.90 \pm (0.07)^{de}$ | $5.53 \pm (0.14)^c$ |
| (4) With 10% un-degraded date pits | $6.02 \pm (0.12)^d$ | $1.48 \pm (0.11)^c$ | $0.95 \pm (0.07)^d$ | $1.67 \pm (0.09)^d$ | $4.61 \pm (0.16)^d$ |
| (5) With 5% degraded date pits | $4.99 \pm (0.11)^e$ | $0.61 \pm (0.10)^d$ | $0.10 \pm (0.06)^b$ | $0.78 \pm (0.11)^c$ | $3.06 \pm (0.17)^e$ |
| (6) With 10% degraded date pits | $3.95 \pm (0.12)^b$ | $0.05 \pm (0.05)^b$ | $0.06 \pm (0.04)^b$ | $0.25 \pm (0.09)^a$ | $2.21 \pm (0.13)^b$ |

The values in Table 3 are means of 6 replicates for each treatment and the values in parentheses are the standard error of the mean. Values with the same letter within a column are not significantly (P>0.01) different according to Fisher's Protected LSD Test.

Chicken gut samples from Group 1 (control group without antibiotics added) had significantly higher (P<0.01) higher total microbial populations than the chicken gut samples fed degraded and un-degraded date pits treatments (group 3, 4, 5, and 6) as well as the control diet with added tetracyclin antibiotic (group 2).

The estimated total populations of total aerobic bacteria, *Escherichia coli, Salmonella* spp., *Shigella* spp. and *Camplyobacter* spp. are significantly (P<0.01) lower in the samples with degraded and un-degraded date pits (groups 3, 4, 5, and 6) compared to the sample without date pits (group 1). There are also significant (P<0.01) decreases in microbial populations by increasing the concentration of date pits.

The treatment which included degraded date pits in 10% concentration (group 6) is significantly superior to other treatments in suppressing microbial population and is shown to provide a reduction in microbial loads equivalent to that achieved by the use of an antibiotic supplemented feed (group 2).

These results show that the degraded date pits could replace conventional antibiotics such as, oxytetracycline-20% in the treatment and prevention of bacterial infections in poultry.

During the trial weight gain and feed intake where measured. The feed conversion ratio (FCR), was calculated. The feed conversion ratio is defined as the amount of feed (in kg) consumed by the animal to produce 1 kg of weight gain. The averaged results per chicken are shown in Table 4.

TABLE 4

| Treatments | Weight-Gain Starter (g) (WGS) | Weight-Gain Total (g) (WGT) | Feed-Intake Starter (g) (FIS) | Feed-Intake Total (g) (FIT) | Feed-Conversion Ratio Starter (FCRS) | Feed-Conversion Ratio Total (FCRT) |
|---|---|---|---|---|---|---|
| (1) Control (without antibiotics) | 866 | 1694.0 | 1200.6 | 1437.0 | 1.387 | 1.557 |
| (2) Control (with antibiotics) | 829.7 | 1729.3 | 1167.5 | 1282.9 | 1.420 | 1.423 |
| (3) With 5% non-degraded date pits | 923.3 | 1778.7 | 1250.1 | 1488.6 | 1.353 | 1.540 |
| (4) With 10% non-degraded date pits | 900.3 | 1729.7 | 1250.9 | 1439.4 | 1.387 | 1.556 |
| (5) With 5% degraded date pits | 835.7 | 1619 | 1199.8 | 1340.5 | 1.450 | 1.570 |
| (6) With 10% degraded date pits | 840 | 1652.7 | 1214.6 | 1387.2 | 1.450 | 1.573 |

The total weight gain from groups 5 and 6 (degraded date pits) were not significantly difference (P>0.05) from the group 2 (control group with antibiotics added). There was no significant difference on body weight gain in the poultry when degraded date pits were added to the feed composition to treat and prevent bacterial infections.

These results show that the treatment and prevention of bacterial infections in poultry can be achieved by replacing part of a conventional feed composition with degraded date pits, as an alternative to using conventional antibiotics, whilst still achieving substantially the same weight gains and FCR as achieved when conventional antibiotics are administered.

Further changes can be made within the scope of the invention. For example other processes can be used to obtain a degraded date pit composition. The degraded date pit compositions can be added to poultry feeds having a different composition. The degraded date pit compositions can be administered to other animals.

What is claimed is:

1. A therapeutic method for treating a bacterial infection in an animal subject in need thereof, the method comprising:
    administering an effective amount of a fungi-degraded date pit composition to the animal subject, wherein the fungi-degraded date pit composition is prepared through solid state degradation, and wherein the bacterial infection is caused by at least one of *Salmonella* genus, *Campylobacter* genus, *Shigella* genus, and *Escherichia coli*.

2. The method according to claim 1, wherein the fungi-degraded date pit composition is administered as part of an animal feed composition.

3. The method according to claim 2, wherein the feed composition comprises between 5-20% w/w of a fungi-degraded date pit composition.

4. The method according to claim 2, wherein the feed composition comprises approximately 10% w/w of a fungi-degraded date pit composition.

5. The method according to claim 1, wherein the fungi-degraded date pit composition comprises mannan-oligosaccharides (MOS).

6. The method according to claim 1, wherein the fungi-degraded date pit composition comprises free mannose.

7. The method according to claim 1, wherein the animal subject is is selected from the group consisting of cattle, horses, pigs, goats, and poultry.

8. The method according to claim 1, wherein the fungi-degraded date pit composition is a *Trichoderma reesei*-degraded date pit composition.

9. A therapeutic method for treating a bacterial infection in an animal subject in need thereof, the method comprising:

administering an effective amount of a *Trichoderma reesei*-degraded date pit composition to the animal subject, wherein the *Trichoderma reesei*-degraded date pit composition is prepared through solid state degradation, and wherein the bacterial infection is caused by at least one of *Salmonella* genus, *Campylobacter* genus, *Shigella* genus, and *Escherichia* coli.

10. The method according to claim 9, wherein the fungi-degraded date pit composition is administered as part of an animal feed composition.

11. The method according to claim 10, wherein the feed composition comprises between 5-20% w/w of a fungi-degraded date pit composition.

12. The method according to claim 10, wherein the feed composition comprises approximately 10% w/w of a fungi-degraded date pit composition.

13. The method according to claim 9, wherein the fungi-degraded date pit composition comprises mannan-oligosaccharides (MOS).

14. The method according to claim 9, wherein the fungi-degraded date pit composition comprises free mannose.

15. The method according to claim 9, wherein the animal subject is selected from the group consisting of cattle, horses, pigs, goats, and poultry.

* * * * *